United States Patent

Bator

[11] Patent Number: 6,057,274
[45] Date of Patent: May 2, 2000

[54] ANTIBACTERIAL COMPOSITION HAVING ENHANCED TACTILE PROPERTIES

[75] Inventor: Patricia E. Bator, Secaucus, N.J.

[73] Assignee: Henkel Corporation, Gulph Mills, Pa.

[21] Appl. No.: 09/119,504

[22] Filed: Jul. 20, 1998

Related U.S. Application Data

[60] Provisional application No. 60/056,739, Aug. 22, 1997.

[51] Int. Cl.[7] .............................. A61K 7/50; C11D 7/50; C11D 17/00; C11D 3/37; C11D 9/00
[52] U.S. Cl. ...................... 510/130; 510/131; 510/470; 510/502; 510/426
[58] Field of Search ................................ 510/130, 135, 510/131, 137, 138, 426, 470, 502; 424/401

[56] References Cited

U.S. PATENT DOCUMENTS

| | | | |
|---|---|---|---|
| 5,646,100 | 7/1997 | Haugk et al. | 510/131 |
| 5,653,970 | 8/1997 | Vermeer | 424/70.24 |
| 5,665,364 | 9/1997 | McAtee et al. | 424/401 |
| 5,716,626 | 2/1998 | Sakurai et al. | 424/401 |
| 5,811,111 | 9/1998 | McAtee et al. | 424/401 |
| 5,833,999 | 11/1998 | Trinh et al. | 424/401 |
| 5,883,059 | 3/1999 | Furman et al. | 510/130 |

*Primary Examiner*—Necholus Ogden
*Attorney, Agent, or Firm*—John E. Drach; Steven J. Trzaska

[57] ABSTRACT

A liquid cleaning composition containing: (a) at least one surfactant, other than a nonionic sugar surfactant; (b) an antibacterial agent; (c) a nonionic sugar surfactant; and (d) a glyceride component.

29 Claims, No Drawings

ANTIBACTERIAL COMPOSITION HAVING ENHANCED TACTILE PROPERTIES

CROSS-REFERENCE TO RELATED APPLICATIONS

This application claims the benefit of earlier filed and copending provisional application Ser. No. 60/056,739, filed on Aug. 22, 1997, the entire contents of which are incorporated herein by reference.

STATEMENT REGARDING FEDERALLY SPONSORED RESEARCH OR DEVELOPMENT

Not Applicable.

BACKGROUND OF THE INVENTION

The present invention generally relates to an antimicrobial composition. More particularly, the invention relates to an antimicrobial composition having tactile properties.

Industrial antimicrobial agents are chemical compositions that are used to prevent microbiological contamination and deterioration of commercial products, materials and systems. The following chemical classes of antimicrobial agents are recognized in industry applications: phenolics; halogen compounds, quaternary ammonium compounds; metal derivatives; amines; alkanolamines and nitro derivatives; anilides; and organo-sulfur and sulfur-nitrogen compounds.

A given antimicrobial agent may either destroy all of the microbes present or just prevent their further proliferation to numbers that would be significantly destructive to the substrate or system being protected. The terms, microbes and microorganisms, refer primarily to bacteria and fungi. Each of these groups is subdivided into two general subclasses: gram-positive and gram-negative bacteria, and among the fungi, molds and yeasts.

Areas of application for antimicrobial agents include cosmetics, disinfectants and sanitizers, wood preservation, food and animal feeds, paint, cooling water, metalworking fluids, hospital and medical uses.

Conventional antimicrobial agents, however, when incorporated into cleaning compositions containing anionics, cationics, nonionics, amphoterics, zwitterionics, and the like, while effective at removing soil particles from substrates being cleaned therewith, also have a tendency of de-fatting human skin, leaving it dry, taught and chapped feeling.

BRIEF SUMMARY OF THE INVENTION

The present invention is directed to a liquid cleaning composition containing:

(a) at least one surfactant, other than a nonionic sugar surfactant;
(b) an antibacterial agent;
(c) a nonionic sugar surfactant; and
(d) a monoglyceride.

The present invention is also directed to a process for making a liquid cleaning composition involving the steps of:

(a) providing a primary mixture containing:
   (i) at least one surfactant, other than a nonionic sugar surfactant; and
   (ii) an antibacterial agent;

(b) providing a secondary mixture containing:
   (iii) a nonionic sugar surfactant; and
   (iv) a monoglyceride; and (c) cold mixing the primary and secondary mixtures to form a cleaning composition.

The present invention is also directed to a process for enhancing the tactile properties of a liquid antibacterial composition, wherein the antibacterial composition contains at least one surfactant, other than a nonionic sugar surfactant and an antibacterial agent, involving adding to the antibacterial composition an effective amount of a mixture of a nonionic sugar surfactant and a monoglyceride.

BRIEF DESCRIPTION OF THE SEVERAL VIEWS OF THE DRAWING

Not Applicable.

DETAILED DESCRIPTION OF THE INVENTION

Other than in the operating examples, or where otherwise indicated, all numbers expressing quantities of ingredients, or reaction conditions, are understood as being modified in all instances by the term "about".

The surfactant component of the present invention is generally selected from the group consisting of anionics, nonionics, cationics, amphoterics and zwitterionics. A typical listing of the classes and species of these surfactants is given in U.S. Pat. No. 3,664,961, the entire contents of which is hereby incorporated by reference. These surfactants can be used individually or in combination at levels in the range of from about 8 to about 40% by weight, and preferably from about 30 to about 40% by weight, based on the total weight of the aqueous antimicrobial composition.

Suitable anionic surfactants include, but are not limited to, water-soluble salts of alkyl benzene sulfonates, alkyl sulfates, alkyl polyethoxy ether sulfates, paraffin sulfonates, alpha-olefin sulfonates and sulfosuccinates, alpha-sufocarboxylates and their esters, alkyl glyceryl ether sulfonates, fatty acid monoglyceride sulfates and sulfonates, and alkyl phenol polyethoxyether sulfates.

Other suitable anionic surfactants include the water-soluble salts or esters of alpha-sulfonated fatty acids containing from about 6 to about 20 carbon atoms in the fatty acid group and from about 1 to about 10 carbon atoms in the ester group.

A particularly preferred anionic surfactant for use in the present invention is sodium lauryl sulfate.

Suitable nonionic surfactants which may be employed in the present invention include, but are not limited to, polyethylene oxide condensates of alkyl phenol having an alkyl group containing from about 6 to about 12 carbon atoms in either straight or branched-chain configuration, the ethylene oxide being present in amounts equal to from 5 to 25 moles of ethylene oxide per mole of alkyl phenol.

Condensation products of primary or secondary alcohols having from 8 to 24 carbon atoms, with from 1 to about 30 moles of alkylene oxide per mole of alcohol may also be employed.

Suitable amphoteric surfactants include water-soluble derivatives of aliphatic secondary and tertiary amines in which the aliphatic moiety can be straight chain or branched and wherein one of the aliphatic substituents contains from about 8 to 18 carbon atoms and one contains an anionic water-solubilizing group, e.g., carboxy, sulfonate, sulfate, phosphate or phosphonate.

Suitable zwitterionic surfactants include water-soluble derivatives of aliphatic quaternary ammonium phosphonium and sulfonium cationic compounds in which the aliphatic moieties can be straight chain or branched, and wherein one of the aliphatic substituents contains from about 8 to 18 carbon atoms and one contains an anionic water-solubilizing group.

Suitable cationic surfactants include the ammonium surfactants such as alkyldimethyl ammonium halogenides, and those surfactants having the formula:

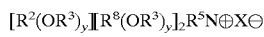

wherein $R^2$ is an alkyl or alkyl benzyl group having from about 8 to about 18 carbon atoms in the alkyl chain, each $R^3$ is selected from the group consisting of $-CH_2CH_2-$, $-CH_2CH(CH_3)-$, $-CH_2CH(CH_2OH)-$, $-CH_2CH_2CH_2-$, and mixtures thereof; each $R^4$ is selected from the group consisting of $C_1-C_4$ alkyl, $C_1-C_4$ hydroxyalkyl, benzyl, ring structures formed by joining the two $R^4$ groups, $-CH_2CHOHCHOHCOR^6$ $-CHOHCH_2OH$ wherein $R^6$ is any hexose or hexose polymer having a molecular weight less than about 1000, and hydrogen when y is not 0; $R^5$ is the same as $R^4$ or is an alkyl chain wherein the total number of carbon atoms of $R^2$ plus $R^5$ is not more than about 18; each y is from 0 to about 10 and the sum of the y values is from 0 to about 15; and X is any compatible anion.

Antibacterial agents which may be employed in the present invention include, but are not limited to, halo-substituted dihydric phenol compounds, specifically, a dihydric phenol 2,4,4'-trichloro-2'-hydroxydiphenyl ether (a.k.a. triclosan) and para chloro meta xylenol (a.k.a. PCMX).

The nonionic sugar surfactants which may be employed in the present invention include, but are not limited to, alkyl polyglycosides and glucamides.

The alkyl polyglycosides which can be used in the process according to the invention correspond to formula I:

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6. Preferred alkyl polyglycosides which can be used in the process according to the invention have the formula I wherein Z is a glucose residue and b is zero. Such alkyl polyglycosides are commercially available, for example, as APG®, GLUCOPON®, or PLANTAREN® surfactants from Henkel Corporation, Ambler, Pa., 19002. Examples of such surfactants include but are not limited to:
1. APG® 225 Surfactant—an alkyl polyglycoside in which the alkyl group contains 8 to 10 carbon atoms and having an average degree of polymerization of 1.7.
2. GLUCOPON® 425 Surfactant—an alkyl polyglycoside in which the alkyl group contains 8 to 16 carbon atoms and having an average degree of polymerization of 1.55.
3. GLUCOPON® 625 Surfactant—an alkyl polyglycoside in which the alkyl group contains 12 to 16 carbon atoms and having an average degree of polymerization of 1.6.
4. GLUCOPON® 325 Surfactant—an alkyl polyglycoside in which the alkyl group contains 9 to 11 carbon atoms and having an average degree of polymerization of 1.6.
5. GLUCOPON® 600 Surfactant—an alkyl polyglycoside in which the alkyl group contains 12 to 16 carbon atoms and having an average degree of polymerization of 1.4.
6. PLANTAREN® 2000 Surfactant—a $C_{8-16}$ alkyl polyglycoside in which the alkyl group contains 8 to 16 carbon atoms and having an average degree of polymerization of 1.4.
7. PLANTAREN® 1300 Surfactant—a $C_{12-16}$ alkyl polyglycoside in which the alkyl group contains 12 to 16 carbon atoms and having an average degree of polymerization of 1.6.

Other examples include alkyl polyglycoside surfactant compositions which are comprised of mixtures of compounds of formula I wherein Z represents a moiety derived from a reducing saccharide containing 5 or 6 carbon atoms; a is a number having a value from 1 to about 6; b is zero; and $R_1$ is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglycosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and polyglycosides, in the resulting product changes and the concentration in the product of the polyglycosides relative to the monoglycoside increases as well as the concentration of individual polyglycosides to the total, i.e., DP2 and DP3 fractions in relation to the sum of all DP fractions. Such compositions are disclosed in U.S. Pat. No. 5,266,690, the entire contents of which are incorporated herein by reference.

Other alkyl polyglycosides which can be used in the compositions according to the invention are those in which the alkyl moiety contains from 6 to 18 carbon atoms one in which the average carbon chain length of the composition is from about 9 to about 14 comprising a mixture of two or more of at least binary components of alkylpolyglycosides, wherein each binary component is present in the mixture in relation to its average carbon chain length in an amount effective to provide the surfactant composition with the average carbon chain length of about 9 to about 14 and wherein at least one, or both binary components, comprise a Flory distribution of polyglycosides derived from an acid-catalyzed reaction of an alcohol containing 6–20 carbon atoms and a suitable saccharide from which excess alcohol has been separated.

A particularly preferred alkyl polyglycoside component for use in the present invention is that of formula I wherein $R_1$ is a monovalent organic radical having from about 8 to about 16 carbon atoms, b is zero, and a is a number having the value 1.55.

The glucamides which can be used in the present invention correspond to formula II:

II wherein $R_3$ is H, $C_1$–$C_4$ hydrocarbyl, 2-hydroxy ethyl, 2-hydroxy propyl, or a mixture thereof, preferably $C_1$–$C_4$ alkyl, more preferably $C_1$ or $C_2$ alkyl, most preferably $C_1$ alkyl (i.e., methyl); and $R_4$ is a $C_5$–$C_{31}$ hydrocarbyl moiety, preferably straight chain $C_7$–$C_{19}$ alkyl or alkenyl, more preferably straight chain $C_9$–$C_{17}$ alkyl or alkenyl, most preferably straight chain $C_{11}$–$C_{19}$ alkyl or alkenyl, or mixture thereof; and Y is a polyhydroxyhydrocarbyl moiety having a linear hydrocarbyl chain with at least 3 hydroxyls directly connected to the chain, or an alkoxylated derivative (preferably ethoxylated or propoxylated) thereof. Y preferably will be derived from a reducing sugar in a reductive amination reaction; more preferably Y is a glycityl moiety. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Y. It should be understood that it is by no means intended to exclude other suitable raw materials. Y preferably will be selected from the group consisting of —$CH_2$—$(CHOH)_n$—$CH_2OH$, —$CH(CH_2OH)$—$(CHOH)_{n-1}$—$CH_2OH$, —$CH_2$—$(CHOH)_2(CHOR')(CHOH)$—$CH_2OH$, where n is an integer from 3 to 5, inclusive, and R' is H or a cyclic mono- or poly-saccharide, and alkoxylated derivatives thereof. Most preferred are glycityls wherein n is 4, particularly —$CH_2$—$(CHOH)_4$—$CH_2OH$. Therefore, when, for example, $R_3$ is methyl, $R_4$ dodecyl; and Y is —$CH_2$—$(CHOH)_4$—$CH_2OH$, the compound in question is referred to as dodecyl N-methylglucamide.

Methods for making glucamides (polyhydroxy fatty acid amides) are known in the art. In general, polyhydroxy fatty acid amides can be made by reductively aminating a reducing sugar reacting with an alkyl amine to form a corresponding N-alkyl polyhydroxyamine and then reacting the N-alkyl polyhydroxyamine with a fatty aliphatic ester or triglyceride to form the N-alkyl, polyhydroxy fatty acid amide. Processes for making polyhydroxy fatty acid amides are disclosed in U.S. Pat. Nos. 1,985,424; 2,965,576; 5,194,639; and 5,334,764, the entire contents of each of which is incorporated herein by reference.

A glyceride is an ester of glycerol and a fatty acid in which one or more of the hydroxyl groups of the glycerol are replaced by an acid radical. The latter may be identical or different so that the glyceride may contain up to three different acid groups. Examples of suitable glycerides for use in the present invention include, but are not limited to, glycerol mono-, di- and tri-oleate, glycerol mono-, di-, and tri-laurate, glycerol mono-, di-, and tri-stearate, and the like. A particularly preferred glyceride for use in the present invention is glycerol monooleate.

According to one embodiment of the present invention, there is provided an aqueous cleaning composition containing: (a) from about 20 to about 50% by weight, preferably from about 25 to about 40% by weight, and most preferably from about 30 to about 35% by weight of a surfactant, other than a nonionic sugar surfactant, preferably an anionic surfactant, and most preferably sodium lauryl sulfate; (b) from about 0.25 to about 0.40% by weight, preferably from about 0.20 to about 0.30% by weight, and most preferably from about 0.20 to about 0.25% by weight of an antibacterial agent; (c) from about 1 to about 15% by weight, preferably from about 3 to about 10% by weight, and most preferably from about 3 to about 5% by weight of a nonionic sugar surfactant, preferably an alkyl polyglycoside; and (d) from about 1.0 to about 5.0% by weight, preferably from about 1.0 to about 3.5% by weight, and most preferably from about 1.0 to about 2.5% by weight of a glyceride, preferably glycerol monooleate.

It should be noted that various auxiliaries typically contained in cleaning compositions may also be added without departing from the spirit of the invention. Examples of suitable auxiliaries include, but are not limited to, hydrotropes, dyes, perfumes, enzymes, chlorine releasing agents, soil suspending agents, thickeners and foam modifiers.

According to another aspect of the present invention, there is also provided a process for making a liquid cleaning composition. The process involves the steps of: (a) providing a primary mixture wherein the primary mixture contains: (i) from about 20 to about 50% by weight, preferably from about 25 to about 40% by weight, and most preferably from about 30 to about 35% by weight of a surfactant, other than a nonionic sugar surfactant, preferably an anionic surfactant, and most preferably sodium lauryl sulfate; and (ii) from about 0.25 to about 0.40% by weight, preferably from about 0.20 to about 0.30% by weight, and most preferably from about 0.20 to about 0.25% by weight of an antibacterial agent. A secondary mixture is then separately formed, wherein the secondary mixture contains: (iii) from about 1 to about 15% by weight, preferably from about 3 to about 10% by weight, and most preferably from about 3 to about 5% by weight of a nonionic sugar surfactant, preferably an alkyl polyglycoside; and (iv) from about 1.0 to about 5.0% by weight, preferably from about 1.0 to about 3.5% by weight, and most preferably from about 1.0 to about 2.5% by weight of a glyceride, preferably glycerol monooleate.

The primary and secondary mixtures, thus formed, are then mixed, without the need for heating either mixture, until a uniform liquid cleaning composition is obtained. The ability to be able to cold mix the liquid cleaning composition of the present invention results in a savings of both time and money since the costs associated with purchasing, running and maintaining heating equipment are avoided.

Another aspect of the present invention relates to a process for enhancing the tactile (skin feel) properties of a liquid antibacterial composition. The process involves adding an effective amount of a surfactant composition containing a nonionic sugar surfactant and a glyceride to an antibacterial composition. The surfactant composition contains from about 50 to about 70% by weight, preferably from about 50 to about 60% by weight, and most preferably from about 50 to about 55% by weight of a nonionic sugar surfactant, preferably an alkyl polyglycoside, and from about 30 to about 50% by weight, preferably from about 30 to about 35% by weight, and most preferably from about 30 to about 33% by weight of a glyceride, preferably glycerol monooleate. This surfactant composition is then added to a liquid antibacterial composition in an amount of from about 3 to about 8% by weight, preferably from about 3 to about 6% by weight, and most preferably from about 3 to about 5% by weight, based on the total weight of the ready-to-use liquid antibacterial composition.

The present invention will be better understood from the examples which follow, all of which are intended for illus-

| Component | Example A | Example B |
| --- | --- | --- |
| STANDAPOL ® WAQ Spec.[1] | 30.00 | 30.00 |
| PLANTAREN ® 1200N | 3.00 | 3.00 |
| LAMESOFT ® PO-65[2] | 3.00 | 3.00 |
| Premix of CETIOL ® HE[3] and Triclosan (1:1) | 0.40 | 0.40 |
| sodium chloride | 1.00 | 1.00 |
| PCMX | — | 0.25 |
| water | q.s. 100 | q.s. 100 |

[1]STANDAPOL ® WAQ Spec. = sodium lauryl sulfate
[2]LAMESOFT ® PO-65 = a mixture of 65% by weight of PLANTAREN ® 818 UP, 32.5% by weight of glycerol oleate and remainder, water.
[3]CETIOL ® HE = PEG-7-glycerol cocoate.

What is claimed is:

1. A liquid cleaning composition comprising:

(a) from about 20 to about 50% by weight, based on the weight of the composition, of at least one surfactant, other than a nonionic sugar surfactant;

(b) an antibacterial agent;

(c) a nonionic sugar surfactant selected from the group consisting of an alkyl polyglycoside corresponding to formula I:

$$R_1O(R_2O)_b(Z)_a \qquad I$$

wherein $R_1$ is a monovalent organic radial having from about 8 to about 16 carbon atoms;
   $R_2$ is divalent alkylene radical having from 2 to 4 carbon atoms; Z is a saccharide residue having 5 or 6 carbon atoms; b is 0; a is a number having a value of about 1.55, a glucamide corresponding to formula II:

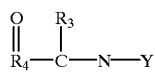

wherein $R_3$ is H, $C_1$–$C_4$ hydrocarbyl, 2-hydroxy ethyl, 2-hydroxy propyl, or a mixture thereof;
   $R_4$ is a $C_5$–$C_{31}$ hydrocarbyl moiety; and Y is a polyhydroxyhydrocarbyl moiety having a linear hydrocarbyl chain with at least 3 hydroxyls directly connected to the chain, or an alkoxylated derivative; and (d) a glyceride component selected from the group consisting of:
   glycerol mono-, di-, and tri-oleate, glycerol mono-, di-, tri-laurate, glycerol mono-, di-, tri-stearate, and mixtures thereof.

2. The composition of claim 1 wherein the surfactant is selected from the group consisting of an anionic surfactant, a nonionic surfactant, a cationic surfactant, an amphoteric surfactant, a zwitterionic surfactant, and mixtures thereof.

3. The composition of claim 2 wherein the surfactant is an anionic surfactant.

4. The composition of claim 3 wherein the anionic surfactant is sodium lauryl sulfate.

5. The composition of claim 1 wherein the antibacterial agent is selected from the group consisting of triclosan, para-chloro-meta-xylenol, and mixtures thereof.

6. The composition of claim 1 wherein the antibacterial agent is present in the composition in an amount of from about 0.20 to about 0.40% by weight, based on the weight of the composition.

7. The composition of claim 1 wherein the nonionic sugar surfactant is the alkyl polyglycoside of formula I.

8. The composition of claim 1 wherein the nonionic sugar surfactant is present in the composition in an amount of from about 3 to about 15% by weight, based on the weight of the composition.

9. The composition of claim 1 wherein the glyceride component is glycerol oleate.

10. The composition of claim 1 wherein the glyceride component is present in the composition in an amount of from about 1.0 to about 5.0% by weight, based on the weight of the composition.

11. A liquid cleaning composition comprising:

(a) from about 30 to about 35% by weight of sodium lauryl sulfate;

(b) from about 0.20 to about 0.25% by weight of an antibacterial agent;

(c) from about 3 to about 5% by weight of an alkyl polyglycoside corresponding to formula I:

$$R_1O(R_2O)_b(Z)_a \qquad I$$

wherein $R_1$ is a monovalent organic radical having from about 8 to about 16 carbon atoms; $R_2$ is a divalent alkylene radical having from 2 to 4 carbon atoms; Z is a saccharide residue having 5 or 6 carbon atoms; b is zero; a is a number having a value of about 1.55; and (d) from about 1.0 to about 2.5% by weight of a glycerol monooleate, all weights being based on the weight of the composition.

12. A process for making a liquid cleaning composition comprising:

(a) from about 20 to about 50% by weight, based on the weight of the composition, of providing a primary mixture containing:
       (i) at least one surfactant, other than a nonionic sugar surfactant; and
       (ii) an antibacterial agent;

(b) providing a secondary mixture containing:
       (iii) a nonionic sugar surfactant; and
       (iv) a glyceride component selected from the group the group consisting of:
       glycerol mono-, di-, and tri-oleate, glycerol mono-, di, tri-stearate, and mixtures thereof; and (c) cold mixing the primary and secondary mixtures to form a cleaning composition.

13. The process of claim 12 wherein the surfactant is selected from the group consisting of an anionic surfactant, a nonionic surfactant, a cationic surfactant, an amphoteric surfactant, a zwitterionic surfactant, and mixtures thereof.

14. The process of claim 13 wherein the surfactant is an anionic surfactant.

15. The process of claim 14 wherein the anionic surfactant is sodium lauryl sulfate.

16. The process of claim 12 wherein the antibacterial agent is selected from the group consisting of triclosan, para-chloro-meta-xylenol, and mixtures thereof.

17. The process of claim 12 wherein the antibacterial agent is present in the composition in an amount of from about 0.20 to about 0.40% by weight, based on the weight of the composition.

18. The process of claim 12 herein the nonionic sugar surfactant is selected from the group consisting of an alkyl polyglycoside corresponding to formula I:

$$R_1O(R_2O)_b(Z)_a \qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6, a glucamide corresponding to formula II:

$$\underset{R_4-\overset{O}{\underset{\|}{C}}-\overset{R_3}{\underset{|}{N}}-Y}{} \qquad II$$

wherein $R_3$ is H, $C_1$–$C_4$ hydrocarbyl, 2-hydroxy ethyl, 2-hydroxy propyl, or a mixture thereof; $R_4$ is a $C_5$–$C_{31}$ hydrocarbyl moiety; and Y is a polyhydroxyhydrocarbyl moiety having a linear hydrocarbyl chain with at least 3 hydroxyls directly connected to the chain, or an alkoxylated derivative.

19. The process of claim 18 wherein the nonionic sugar surfactant is an alkyl polyglycoside.

20. The process of claim 19 wherein in formula I, $R_1$ is a monovalent organic radical having from about 8 to about 16 carbon atoms, b is zero, and a is a number having a value of about 1.55.

21. The process of claim 12 wherein the nonionic sugar surfactant is present in the composition in an amount of from about 3 to about 15% by weight, based on the weight of the composition.

22. The process of claim 12 wherein the glyceride component is glycerol oleate.

23. The process of claim 12 wherein the glyceride component is present in the composition in an amount of from about 1 to about 5% by weight, based on the weight of the composition.

24. A process for enhancing the tactile properties of a liquid antibacterial composition comprising adding an effective amount of a surfactant composition to the antibacterial composition, the surfactant composition comprising:

(a) a nonionic sugar surfactant selected from the group consisting of an alkyl polyglycoside corresponding to formula I:

$$RO(R_2O)_b(Z)_a \qquad I$$

wherein $R_1$ is a monovalent organic radical having from about 8 to about 16 carbon atoms;
$R_2$ is divalent alkylene radical having from 2 to 4 carbon atoms; Z is a saccharide residue having 5 or 6 carbon atoms; b is 0; a is a number having a value of about 1.55, a glucamide corresponding to formula II:

$$\underset{R_4-\overset{O}{\underset{\|}{C}}-\overset{R_3}{\underset{|}{N}}-Y}{} \qquad (II)$$

wherein $R_3$ is H, $C_1$–$C_4$ hydrocarbyl, 2-hydroxy ethyl, 2-hydroxy propyl, or a mixture thereof;
$R_4$ is a $C_5$–$C_{31}$ hydrocarbyl moiety; and Y is a polyhydroxyhydrocarbyl moiety having a linear hydrocarbyl chain with at least 3 hydroxyls directly connected to the chain or an alkoxylated derivative; and (b) a glyceride component selected from the group consisting of:
glycerol mono-, di-, and tri-oleate, glycerol mono-, di-, tri-laurate, glycerol mono-,. di-, tri-stearate, and mixtures thereof.

25. The process of claim 24 wherein the nonionic sugar surfactant is the alkyl polyglycoside of formula I.

26. The process of claim 24 wherein the nonionic sugar surfactant is present in the surfactant composition in an amount of from about 50 to about 65% by weight, based on the weight of the composition.

27. The process of claim 24 wherein the glyceride component is glycerol oleate.

28. The process of claim 24 wherein the glyceride component is present in the surfactant composition in an amount of from about 35 to about 50% by weight, based on the weight of the composition.

29. The process of claim 24 wherein the surfactant composition is added to the liquid antibacterial composition in an amount of from about 3 to about 8% by weight, based on the total weight of the composition.

* * * * *